(12) United States Patent
Coles et al.

(10) Patent No.: US 6,613,030 B1
(45) Date of Patent: Sep. 2, 2003

(54) DISPOSABLE ABSORBENT ARTICLES WITH IMPROVED ADHESIVE FOR SKIN ATTACHMENT

(75) Inventors: Peter Coles, Kriftel (DE); Fabio Cinelli, Bologna (IT); Italo Corzani, Chieti (IT); Hugh Semple Munro, Chipping Camden (GB); Mohammed Yasin, Birmingham (GB)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/744,890

(22) PCT Filed: Jul. 30, 1999

(86) PCT No.: PCT/GB99/02514
§ 371 (c)(1),
(2), (4) Date: Mar. 22, 2001

(87) PCT Pub. No.: WO00/07636
PCT Pub. Date: Feb. 17, 2000

(51) Int. Cl.[7] .................................................. A61F 13/15
(52) U.S. Cl. .................................. 604/385.02; 604/389
(58) Field of Search ................................ 604/317–402

(56) References Cited

U.S. PATENT DOCUMENTS

| | | | | |
|---|---|---|---|---|
| 4,699,146 A | | 10/1987 | Sieverding | |
| 5,670,557 A | | 9/1997 | Dietz et al. | |
| 6,156,818 A | * | 12/2000 | Corzani et al. | 523/111 |
| 6,160,200 A | * | 12/2000 | Ehrnsperger et al. | 604/378 |
| 6,187,989 B1 | * | 2/2001 | Corzani et al. | 602/43 |
| 6,316,524 B1 | * | 11/2001 | Corzani et al. | 523/111 |

FOREIGN PATENT DOCUMENTS

| | | |
|---|---|---|
| EP | 0676457 | 10/1995 |
| GB | 2284767 | 6/1995 |
| WO | WO 9724149 | 7/1997 |

\* cited by examiner

*Primary Examiner*—Jeanette Chapman
(74) *Attorney, Agent, or Firm*—Peter D. Meyer

(57) ABSTRACT

The present invention relates to disposable absorbent articles such as diapers and sanitary napkins which are provided with adhesives for attachment of the article to the skin which adhesives provide secure attachment and are pleasing to the skin upon application, yet cause no discomfort upon removal.

15 Claims, 1 Drawing Sheet

DISPOSABLE ABSORBENT ARTICLES WITH IMPROVED ADHESIVE FOR SKIN ATTACHMENT

FIELD OF THE INVENTION

Figure 1:
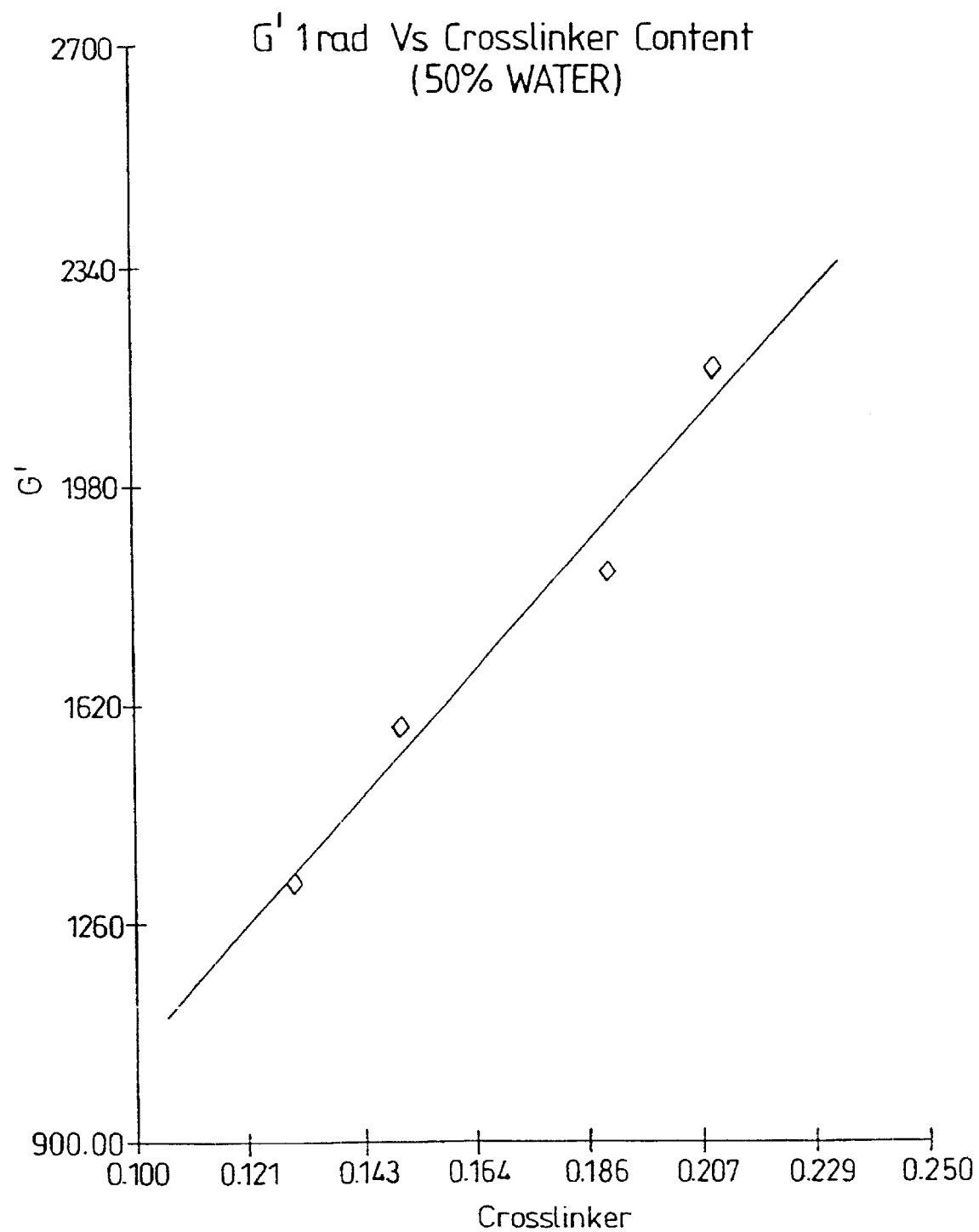

The present invention relates to a disposable absorbent articles such as diapers, sanitary napkins, pantiliners, tampons, perspiration pads, adult incontinence devices and the like to be attached directly to the skin of the wearer. The articles utilise an improved adhesive so as to facilitate easy application and removal of the article from the wearer, whilst ensuring maintenance of the article in the desired position.

BACKGROUND OF THE INVENTION

The present invention relates to adhesives which are particularly useful to absorbent articles for absorption of body liquids which naturally emanate from a body without a wound. For example to attach sanitary napkins or pantiliners in the genital region. Also incontinence devices which are worn e.g. in the genital region or perspiration pads which are worn in the arm pit region of a person can suitably employ the adhesive of the present invention.

Such adhesives have been generally disclosed in for example US statutory invention registration H1602 or WO 96/33683 and WO 95/16424. The latter discloses sanitary articles having a topical adhesive which is applied on the wearer facing side of a sanitary napkin along the entire periphery. WO 96/13238 discloses a topical adhesive which is described in terms of frequency dependency. EP-638 303 discloses the use of a topical adhesive on side cuffs of sanitary napkins in order to keep the cuffs in an upright position. Swiss publication CH-643730 discloses the use of a very long sanitary napkin having chamfered outer edges with a topical adhesive at the four corners of the outer edges in order to provide a topical adhesive area well outside the region of pubic hair growth.

However all of these disclosures typically disclose a product which is designed to be utilised in combination with an undergarment and hence the degree of adhesion actually provided is very low and is not designed to withstand any excessive pressure. Moreover the adhesive is only discussed in general terms or concentrates on the area of application of the adhesive to the article. The nature of adhesive per se other than the basic physical requirements such as pressure sensitivity are not discussed in particular with reference to the chemical composition or the adhesive criteria.

The prior art in the general field of adhesives for attachment to the skin is particularly developed in the field of articles such as band-aids, plasters and bandages. These articles are however typically applied in an emergency situation, where for example, a cut into the skin of the wearer has occurred and absorption of the body liquids emanating from a wound is desired. In this context performance aspects of the article such as easy application and use of the product, comfortable wear as well as painless removal, and discreteness are again subordinate, to other criteria in this case such as sterility, healing support, and mechanical protection of the wound. Also such wound covering absorbent articles are mostly adhered to the skin where prior to application of the absorbent article bodily hair can be removed or where little hair grows.

In order to provide the desired level of adhesion of such bandages, the prior art typically discloses the utilisation of certain adhesives having very high cohesive strengths such as rubber based adhesives and acrylics. These adhesives are then applied as thick layers to maximise the adhesive force by which the bandage is secured to the skin of the wearer.

U.S. Pat. No. 4,699,146 discloses hydrophilic elastomeric pressure sensitive adhesives suitable for use with ostomy devices, bandages, ulcer pads, sanitary napkins, diapers, and althetic padding. The adhesive comprises at least 1 uradiation cross linked organic polymer and an adhesive plasticizer.

GB 2 115 431 discloses adhesives for bandages, wounds or burn dressings, EKG adhesives, sanitary napkins, diapers and ulcer pads. The adhesive comprises an uradiation cross linked organic polymer such as polyvinylpyrrolodine and an adhesive plasticizer.

However, for application such as absorbent articles it is important that the adhesive has a skin compatible composition and not be harsh or aggressive towards the skin or cause skin irritation or inflammation. Also it is preferred if the adhesive is compliant with the skin of the wearer such that maximum skin surface contact between the adhesive and the skin is achieved. Moreover, it is also desirable to provide an adhesive such that the absorbent article can be readily removed from the wearer, without the wearer experiencing any unacceptable pain level. This is particularly important under circumstances, where the article is removed and reapplication of the article once or even a number of times is required for example to allow for urination and or to ensure the application of such articles on sensitive skin and wearer groups such as infants. However, on the other hand the desired level of adhesion, albeit painless should of course also be maintained during such multiple applications of the article.

Hence there exists a need to disposable absorbent articles having an adhesive for the secure attachment and painless removal of the article from the skin suitable for use of sensitive skin of an infant and or of the genitalia and it is thus an object of the present invention to provide such an article.

It is another objective of the present invention to provide an adhesive that exhibits an ability to adhere to skin upon reapplication, particularly multiple reapplication for example when the article is removed for urination purposes or is misplaced, whilst still allowing painless removal.

It is another object of the present invention to provide an adhesive which upon removal from the skin of the wearer leaves no residues. It is yet another object of the present invention to provide an adhesive which does not cause a cold or otherwise unacceptable temperature sensation upon application to the wearer.

An additional object of the present invention to provide an adhesive which provides flexibility, stretchability and contractability so that it is able to adapt to the contours of the body during all bodily movements and hence be comfortable for the wearer of the article, whilst still having sufficient adhesive capacity to ensure secure attachment during use.

It has now been surprisingly found that the above drawbacks will be substantially alleviated by providing the absorbent article with an adhesive as defined hereinafter. The adhesive provides secure attachment, is pleasing to the skin upon application, and yet causes no discomfort upon removal and maintains its adhesive strength over the period of wear even under exposure to excess liquids.

SUMMARY OF THE INVENTION

According to the invention there is provided a disposable absorbent article in association with the adhesive as defined herein:

The adhesive allows attachment of disposal absorbent articles to the skin of the wearer, the adhesive being provided as a layer having a certain thickness or calliper C measured in millimeters (mm), typically on at least part of the wearer facing surface of the article.

Detailed analysis of the sequence of common situations occurring from the application of absorbent articles to the time of removal of such articles has shown that specific adhesive characteristics need to be preferably satisfied in order to achieve the desired performance objectives, in particular to secure initial attachment, secure attachment during use and painless removal after wear. The characteristics which have been considered in this context are the elastic modulus describing the elastic; behaviour of the material and the viscous modulus which describes the viscous behaviour of the adhesive material.

The viscous behaviour of the adhesive can be interpreted to represent an indication of the ability of the adhesive to quickly attach and securely adhere to a particular surface. The elastic behaviour can be interpreted as an indication of the "hardness" behaviour of the adhesive. Its value is also important for good initial attachment. Their combination is believed to be an indicator of the required force upon removal. The relation between elastic and viscous modulus is considered to be an indication on which fraction of the removal energy will be dissipated within the adhesive and which fraction is available to trigger the actual removal.

In order to provide adhesives for secure initial and prolonged attachment and easy/painless removal the relation between the elastic modulus and the viscous modulus as well as their dynamic behaviour is also of importance.

The adhesive has an elastic modulus at a temperature of 37° C. (100° Fahrenheit) abbreviated $G'_{37}$, a viscous modulus at a temperature of 37° C. (100° Fahrenheit) of $G''_{37}$, and a viscous modulus at a temperature of 25° C. (77° Fahrenheit) of $G''_{25}$.

The adhesive used in the present invention preferably satisfies the following conditions;

$G'_{37}$ (1 rad/sec) is in the range 500 Pa to 20000 Pa, preferably 700 Pa to 15000 Pa, most preferably 1000 Pa to 10000 Pa.

$G''_{37}$ (1 rad/sec) is in the range 100 Pa to 15000 Pa, preferably 100 Pa to 10000 Pa, most preferably 300 Pa to 5000 Pa.

and the ratio of $G'_{37}$ (1 rad/sec) / $G''_{37}$ (1 rad/sec) is in the range of 1 to 30.

Provided the above rheological conditions are satisfied the adhesives will also satisfy conditions such as sufficient cohesiveness (to prevent residue of adhesive on the skin) which are important for commercial use of such adhesives and apparent to those skilled in the art. Adhesive compositions which satisfy the above criteria can be used as adhesives for the article provided they also satisfy the common requirements of being safe for use on human or animal skin during use and generally after disposal of the article.

Often the criteria of hygienic appearance such that adhesive compositions which are transparent or white upon application are preferred.

It has been determined that the relation between the thickness or calliper C, measured in millimeters (mm), of the layer in which the adhesive is provided, typically onto at least a portion of the wearer facing surface of the article, and the viscous modulus $G''_{25}$ at about 100 rad/sec of the adhesive, is relevant to the scope of providing an easy and painless removal from the wearer's skin of such a adhesive applied on at least a portion of the wearer facing surface of an absorbent article for attachment of said article to the skin of a wearer.

The adhesive used in the present invention is thus preferably provided as a layer having a thickness C such that the viscous modulus $G''_{25}$ (100 rad/sec) and the thickness C preferably satisfy the following empirical equation:

$$G''_{25} \leq [(7.00+C) \times 3000] Pa$$

and preferably also the following empirical equation:

$$G''_{25} \leq [(5.50+C) \times 1700] Pa$$

DETAILED DESCRIPTION OF THE INVENTION

According to the present invention the adhesive can be utilised on disposable absorbent articles such as diapers, sanitary napkins, panty liners, incontinence devices, perspiration pads and tampons. The word "skin" according to the present invention does not only relate to the specific derma of the user but includes the mucous tissue as well as the hair which is typically found in the genital region.

The adhesive is provided with the preferred pattern, typically on the wearer facing surface of the article, as a layer having a thickness or calliper C that is preferably constant. The layer can be preferably continuous or alternatively discontinuous, e.g. in form of dots, spirals, or stripes.

Even though adhesives are used like pressure sensitive adhesives on human skin hair and mucous tissues, it is understood that the topical adhesive compositions could only with difficulty be considered typical pressure sensitive adhesives (referred to as PSA hereinafter) on the basis of the most characteristic rheological behaviours identifying such materials.

In fact as the person skilled in the art of adhesives knows, the most characteristic feature that distinguishes a PSA from other substances that can temporarily adhere objects (e.g. water between two glass plates could) is the fact that their rheological parameters and especially the Elastic Modulus G' vary greatly with the frequency of applied stresses. More in particular, G' of PSA can increase over some orders of magnitude, while the frequency of applied stresses varies from typical bonding frequency to typical debonding frequency, i.e. 1 rad/s to 100 rad/s as indicated below.

As a first consequence, it is therefore inadmissible to define materials intended for use as "adhesives" by giving values of rheological parameters and especially of G' at a fixed value of frequency. This can be misleading because in the absence of other characteristics it will include materials which have no practical value. It is hence necessary that rheological characterisation must be on the basis of dynamic considerations. This not only applies to the Elastic Modulus G' but also to the viscous modulus G" and hence also for tan (d)=G"/ G'.

It is well known that typical PSAs have not only a high variation of G' across the considered frequencies, but also that there is an even higher variation of G" which can get close or become even higher than the value of G', i.e. tan (d) becomes about or even greater than 1, in particular at the frequencies that are typical of debonding.

Without wishing to be bound by theory this can be interpreted as meaning that a high fraction of the energy applied for the debonding is dissipated within the adhesive (so it is not effective in causing the debonding) and through the interface of the adhesive and the skin, while this fact causes macroscopically the recording of a very high level of adhesive force.

As indicated above materials useful as adhesives for use in the present invention have rheological characteristics which are measured at a reference temperature of 37° C. (as usual body temperature of humans) and in a range of frequencies. It has been found that upon application of a disposable absorbent article with a adhesive the adhesive contact is formed at a low frequency, while debonding happens at the speed of removing the article. This speed is expressed as a frequency of 100 rad/s, while the low frequency of forming the adhesive bond has been found to be on the order of 1 rad/s. Therefore, the frequency range for use according to the present invention is between 1 and 100 rad/s.

In order to provide good conditions of bonding, i.e. at a frequency of about 1 rad/sec, the absolute values of the elastic modulus should not be too high, otherwise the adhesive is too hard and it is not able to intimately join or mold to the surface to which it is expected to adhere. It is also important to have a low absolute value of G" in order to have good cohesion while the material remains soft and capable of gently adhering to skin.

The ratio of $G'_{37}$ (1 rad/sec) over $G''_{37}$ (1 rad/sec) is important to ensure that these two values are balanced upon adhesion to the skin.

Importantly, the ratio of $$\frac{G'_{37}(100\ \text{rad/sec}) - G''_{37}(100\ \text{rad/sec})}{G'_{37}(1\ \text{rad/sec}) - G''_{37}(1\ \text{rad/sec})}$$

needs to be large enough to ensure that the dynamic behaviour of both the elastic and the viscous module are maintained in a relationship which provides secure adhesion and painless and easy removal.

Finally the person skilled in the art will also recognise that the Glass Transition Temperature Tg of the adhesive composition, the specific heat capacity, and the specific heat conductivity are parameters which are useful to more fully define the group of useful adhesives.

The following set of characteristics should preferably be satisfied for the adhesive for use in the present invention:

| | |
|---|---|
| $G_{37}'$ (1 rad/sec) | is in the range 500 Pa to 20000 Pa, preferably 700 Pa to 15000 Pa, most preferably 1000 Pa to 10000 Pa. |
| $G_{37}''$ (1 rad/sec) | is in the range 100 Pa to 15000 Pa, preferably 100 Pa to 10000 Pa, most preferably 300 Pa to 5000 Pa. |
| the ratio of $G_{37}'$ (1 rad/sec)/$G_{37}''$ (1 rad/sec) is in the range of 1 to 30. | |
| the ratio | $\frac{G'_{37}(100\ \text{rad/sec}) - G''_{37}(100\ \text{rad/sec})}{G'_{37}(1\ \text{rad/sec}) - G''_{37}(1\ \text{rad/sec})}$ |
| | is not less than 0.5, preferably in the range 0.7 to 3, most preferably in the range 1 to 1.8. |

The value of the ratio of $G'_{37}/G''_{37}$ at least for the frequency range above 1 rads/up to 100 rads/s should preferably be not less than 0.5, preferably from 0.7 to 10 and most preferably from 1 to 7.

The rheological behaviour can also be related to the values of the Glass Transition Temperature Tg. For topical adhesives for use in the present invention Tg should preferably be less than 0° C., more preferably less than −5° C. and most preferably less than −10° C.

In order to provide adhesive compositions which satisfy the requirements of the above rheological and physical characteristics of an adhesive any medically suitable substantially water insoluble pressure sensitive adhesives comprising a polymer which forms a 3-dimensional matrix meeting the these characteristics may be utilised.

According to the present invention the 3 dimensional matrix also referred to herein as a gel, comprises as an essential component a polymer which can be physically or chemically cross linked. The polymer may be naturally or synthetically derived. The uncrosslinked polymer includes repeating units or monomers derived from vinyl alcohols, vinyl ethers and their copolymers, carboxy vinyl monomer, vinyl ester monomers, esters of carboxy vinyl monomers, vinyl amide monomers, anionic vinyl monomers, hydroxy vinyl monomers, cationic vinyl monomers containing amines or quaternary groups, N-vinyl lactam monomer, polyethylene oxides, polyvinylpyrrolidone (PVP), polyurethanes, acrylics such as methyl acrylate, 2-hydroxyethyl methacrylate, methoxydiethoxyethyl methacrylate and hydroxydiethoxyethyl methacrylate, acrylamides, and sulphonated polymers such as acrylamide sulphonated polymers for example 2 acrylamido methylpropane sulphonic acid and acrylic (3-sulphopropyl) ester acid, and mixtures thereof. Also acrylonitrile, methacrylamide, N,N,-dimethylacrylamide, acrylic esters such as methyl, ethyl and butyl acrylates. Alternatively, the uncrosslinked polymer may be a homopolymer or copolymer of a polyvinyl ether, or a copolymer derived from a half ester of maleic ester. Similarly any other compatible polymer monomer units may be used as copolymers such as for example polyvinyl alcohol and polyacrylic acid or ethylene and vinyl acetate.

As another alternative, the polymers may be block copolymer thermoplastic elastomers such as ABA block copolymers such as styrene-olefin-styrene block copolymers or ethylene-propylene block copolymers. More preferably such polymers include hydrogenated grade styrol/ethylene-butylene/styrol (SEBS), styrene/isoprene/styrene (SIS), and styrol/ethylene-propylene/styrol (SEPS).

Particularly preferred polymers are acrylics, sulphonated polymers such as acrylamide sulphonated polymers, vinyl alcohols, vinyl pyrrolidone, polyethylene oxide and mixtures thereof. Most preferred are nitrogen containing polymers.

According to the present invention the 3 dimensional adhesive matrix also essentially comprises a plasticiser, which is preferably a liquid at room temperature. This material is selected such that the polymer may be solubilized or dispersed within the plasticiser. For embodiments wherein irradiation cross linking is to be carried out, the plasticiser must also be irradiation cross linking compatible such that it does not inhibit the irradiation cross linking process of the polymer. The plasticiser may be hydrophilic or hydrophobic.

Suitable plasticisers include water, alcohols, polyhydric alcohols such as glycerol and sorbitol, and glycols and ether glycols such as mono- or diethers of polyalkylene gylcol, mono- or diester polyalkylene glycols, polyethylene glycols (typically up to a molecular weight of about 600), glycolates, glycerol, sorbitan esters, esters of citric and tartaric acid, imidazoline derived amphoteric surfactants, lactams, amides, polyamides, quaternary ammonium compounds, esters such phthalates, adipates, stearates, palmitates, sebacates, or myristates, and combinations thereof. Particularly preferred are polyhydric alcohols, polyethylene glycol (with a molecular weight up to about 600), glycerol, sorbitol, water and mixtures thereof.

Typically the adhesive comprises a ratio of polymer to plasticiser by weight of from 1:100 to 100:1, more preferably from 50:1 to 1:50. However, the exact amounts and ratios of the polymer and plasticiser will depend to a large extent on the exact nature of polymer and plasticisers utilised and can be readily selected by the skilled person in the art. For example a high molecular weight polymer material will require a greater amount of plasticiser than a low molecular weight polymer.

Other common additives known in the art such as preservatives, antioxidants, pigments, mineral fillers and mixtures thereof may also be comprised within the adhesive composition in quantities up to 10% by weight each respectively.

According to the present invention the polymer component of the adhesive can be physically or chemically cross linked in order to form the 3 dimensional matrix. Physical cross linking refers to polymers having cross links which are not chemical covalent bonds but are of a physical nature such that there are areas in the 3 dimensional matrix having high crystallinity or areas having a high glass transition temperature. Chemical cross linking refers to polymers which are linked by chemical bonds. Preferably the polymer is chemically cross linked by radiation techniques such as thermal-, E beam-, UV-, gamma or micro-wave radiation.

In addition when chemical crosslinks are formed in the system, a polyfunctional cross linker and/or a free radical initiator may be present in the premix to initiate the crosslinking upon irradiation. Such an initiator can be present in quantities up to 5% by weight, preferably from 0.02% to 2%, more preferably from 0.02% to 0.2%. Suitable photoinitiators include type 1-α-hydroxy-betones and benzilidimethyl-betols e.g. Irgocure 651 which are believed to on irradiation to form benzoyl radicals that initiate polymerization. Particularly preferred is l-hydroxycyclohexylphenylketone (available under the trade name Irgacure 184 from Ciba Speciality Chemicals). In addition from 0.02% to 2% of thermal initiators may also be used.

The performance of hydrogels as adhesives is related to the surface energetics of the adhesive and of the adherend (for example mammalian skin) and to the viscoelastic response of the bulk adhesive. The requirement that the adhesive wets the adherend to maximise the work of adhesion is well known. This requirement is generally met when the adhesive has a similar or lower surface energy to the adherend. The viscoelastic properties, in particular the elastic or storage modulus (G') and the viscosity modulus (G") are important. They are measured by dynamic mechanical testing at different rad/s. Their values at low rad/s (approximately 0.01 to 1 rad/s) and high rad/s (100 to 1000 rad/s) has been related to the wetting/creep behaviour and peel/quick stick properties respectively. The choice, assembly and processing of the ingredients of the hydrogel adhesive are usually targetted at making a material with a balance of properties suitable for pressure sensitive adhesive applications. A balance between the quantities and nature of polymer, plasticiser and the degree of crosslinking/entanglement has to be achieved.

When water is lost from the hydrogel the adhesive properties are likely to change deleteriously. Whilst the presence of glycerol or other polyhydric alcohols in other reported formulations has been quoted to provide humectant properties to the hydrogel, it has been found that the most important parameter to preventing water loss is the activity of the water within the hydrogel which in turn depends on the nature and proportions of the other components and manner of processing.

Water activity in the hydrogel adhesive is primarily dependent on the water content and the nature of the polymeric components and the way in which they are processed. Water activity has been shown to have a better correlation with the growth of bacteria and moulds than water content. It has been found that organisms struggle to grow at water activities less than 0.8. Enzyme activity has also been reported to decrease significantly below activity of 0.8. Water activity has also been found to influence the adhesivity of the hydrogel adhesive in that at water activities above about 0.75, they become less adhesive. A bioadhesive composition having a suitable balance of the characteristics discussed above has now surprisingly been found.

According to the invention there is provided a bioadhesive composition characterised in that it has:
 (i) a water activity of from 0.4 to 0.9;
 (ii) an elastic modulus at 1 rad/s of from 700 to 15,000 Pa;
 (iii) an elastic modulus at 100 rad/s of from 2000 to 40,000 Pa;
 (iv) a viscous modulus at 1 rad/s of from 400 to 14,000 Pa;
 (v) a viscous modulus at 100 rad/s of from 1000 to 35,000 Pa;
wherein the viscous modulus is less than the elastic modulus in the frequency range of from 1 to 100 rad/s.

Examination of the rheological properties of the compositions have been successfully used to characterise and differentiate adhesive behaviour. Typically the elastic modulus (G') and the viscous modulus (G") are measured over a range of 0.01–100 rad/s at a given temperature. For skin applications the appropriate temperature is 37° C. The moduli at low rad/s values relate to the initial bonding of the adhesive to skin and the higher to the changes in moduli values associated with de-bonding. Methods of measuring G' and G" are well known; for example a Rheometric Scientific RS-5 rheometer could be used.

The water activity of the composition can be measured using impedance methods with devices such as the Rotronic AWVC (manufactured by Rotronic). The activity of water may also be determined by placing the composition in environments of controlled humidity and temperature and measuring the changes in weight. The relative humidity (RH) at which the composition does not change weight corresponds to the activity of water in the gel (RH/100). The use of saturated salt solutions to provide the appropriate environmental conditions is well known. All compositions directly exposed to relative humidities less than that corresponding to the activity of water will be thermodynamically allowed to lose water. Exposure to greater relative humidities and the composition will gain weight.

The bioadhesive composition preferably comprises an aqueous plasticiser, a copolymer of a hydrophilic unsaturated water-soluble first monomer and a hydrophilic unsaturated water-soluble second monomer and a cross-linking agent, the first monomer having a tendency preferentially to enhance the bioadhesive properties of the composition.

Preferably the first monomer has a tendency also to enhance the mechanical strength of the composition according to the invention and/or the second monomer has a tendency preferentially to increase the water activity of the composition.

The bioadhesive composition is preferably obtainable by polymerising an aqueous reactive mixture comprising the said first monomer, the said second monomer and a crosslinking agent.

According to the invention there is further provided a biomedical electrode which comprises a bioadhesive composition according to the invention in association with an electrically conductive interface. The biomedical electrode optionally further comprises a support. The electrically conductive interface preferably comprises a layer of electrically conductive material which is preferably applied to the support, when present.

The invention also provides a fixation product suitable for attaching a biomedical device to skin (or the human body) e.g. a catheter, tubing, wires or cables which product comprises a bioadhesive composition according to the invention.

In preferred embodiments the first and second monomers will be acrylate based monomers selected for their ability to polymerise rapidly in water and having substantially the same molecular weight whereby in a mixture of the two the relative proportions may be varied without significantly altering the molar characteristics of the composition.

The first monomer is preferably a compound of formula

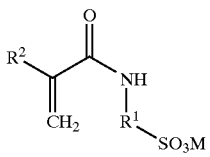

(I)

wherein $R^1$ is an optionally substituted hydrocarbon moiety, $R^2$ is hydrogen or optionally substituted methyl and ethyl, and M represents hydrogen or a cation.

$R^1$ is preferably an optionally substituted alkyl, cycloalkyl or aromatic moiety. Preferably $R^1$ represents a saturated moiety or an aromatic moiety. $R^1$ preferably contains from 3 to 12 carbon atoms, more preferably from 3 to 6 carbon atoms. A preferred moiety which $R^1$ represents is

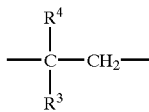

wherein $R^3$ represents hydrogen or an optionally substituted straight or branched chain alkyl group possessing from 1 to 6 carbon atoms and $R^4$ represents an optionally substituted straight or branched chain alkyl group possessing from 1 to 6 carbon atoms.

The second monomer is preferably a compound of formula

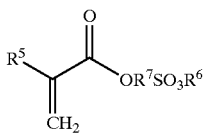

(II)

wherein $R^5$ represents hydrogen or optionally substituted methyl or ethyl, $R^6$ represents hydrogen or a cation and $R^7$ represents an optionally substituted alkyl moiety of 1 to 4 carbon atoms. Preferably $R^7$ represents optionally substituted n-propyl.

$R^1$, $R^2$, $R^3$, $R^4$, $R^5$ and $R^7$ are optionally substituted by a group which preferably has a tendency to increase the water solubility of the compound. Suitable groups will be well known to a person of skill in the art. A preferred optional substituent is a hydroxyl, amino or ammonium group or a halogen (e.g. chlorine, bromine, or iodine) atom. A suitable cation is an alkali metal cation, especially sodium or potassium.

Most preferably the first monomer is 2-acrylamido-2-methylpropanesulphonic acid or an analogue thereof or one of its salts, e.g. an alkali metal salt such as a sodium, potassium or lithium salt, while the second monomer is a polymerisable sulphonate or a salt, e.g. an alkali metal salt such as a sodium, potassium or lithium salt, of acrylic acid (3-sulphopropyl)ester or an analogue thereof. Particular preferred examples of these respective monomers are the sodium salt of 2-acrylamido-2-methylpropanesulphonic acid, commonly known as NaAMPS, and acrylic acid (3-sulphopropyl)ester potassium salt, commonly known as SPA. NaAMPS is available commercially at present from Lubrizol as either a 50% aqueous solution (reference code LZ2405) or a 58% aqueous solution (reference code LZ2405A). SPA is available commercially in the form of a solid from Raschig.

The total monomer content in the aqueous reactive mixture is preferably from 15% to 60% by weight, preferably from 20% to 50% by weight.

In preferred embodiments the ratio by weight of the first monomer to the second monomer is from 20:1 to 2:3, preferably 10:1 to 2:3; more preferably in the range 60:40 to 40:60, and may sometimes be approximately 50:50.

The first monomer is preferably included in an amount by weight of from 1% to 60%, more preferably from 5% to 50%, most preferably from 15% to 40%. The second monomer is preferably included in an amount by weight of from 1% to 50%, preferably from 10% to 30%, most preferably from 10% to 20%. The crosslinker is preferably included in an amount of from 0.01% to 2%, more preferably from 0.1 to 2% by weight. The balance of the composition preferably comprises an aqueous plasticiser.

One advantage of the first and second monomers is that it has been found that high monomer content solutions can be achieved (approximately 75%). It has also been found that the second monomer is soluble in polyhydric alcohols such as glycerol, and addition of glycerol to the first and second monomer mixture enhances the solubilisation process. It has been found that the combination of the two monomers enables a greater control over water content than can be achieved otherwise. This can be important because it has also been found that compositions made with the final water content as an integral part of the pre-gel mix have different properties from those made with an excess of water and then dried to the final composition. For example, hydrogels with a final composition obtained by the evaporation of water generally have lower elastic or storage moduli than those made with no evaporation of water. To obtain similar levels of elastic moduli, the amount of crosslinker required in the former materials is higher. The evaporation of water and extra crosslinker add to the cost of the process. This problem is avoided by the present invention where a final drying step is generally not required.

Conventional crosslinking agents are used to provide the necessary mechanical stability and to control the adhesive properties of the composition. Although compositions can be made with suitable adhesive and electrical properties, a sufficient amount of a suitable cross-linker must be used; if too little crosslinker is used, converting the material into a completed electrode becomes impossible. Typical crosslinkers include tripropylene glycol diacrylate, ethylene glycol dimethacrylate, alkoxylated triacrylate, polyethylene glycol diacrylate (PEG400 or PEG600), methylene bis acrylamide.

The aqueous reactive mixture optionally further comprises a surfactant, an additional monomer, a processing aid (which is preferably a hydrophobic polymer), a water soluble polymer suitable for forming an interpenetrating polymer network, a non-hydrophilic polymer, and/or an antimicrobial agent (e.g. citric acid, stannous chloride).

The process used to prepare bioadhesive compositions in accordance with the invention comprises mixing the ingredients to provide a reaction mixture in the form of an initial pre-gel aqueous based liquid formulation, which is then converted into a gel by a free radical polymerisation reaction. This may be achieved for example using conventional thermal initiators and/or photoinitiators or by ionizing radiation. Photoinitiation is a preferred method and will usually be applied by subjecting the pre-gel reaction mixture containing an appropriate photoinitiation agent to UV light after it has been spread or coated as a layer an siliconised release paper or other solid substrate. The processing will generally be carried out in a controlled manner involving a precise predetermined sequence of mixing and thermal treatment or history. One preferred feature of the process according to the invention is that no water is removed from the hydrogel after manufacture.

Additional Monomer

The composition according to the invention preferably comprises one or more additional monomers. A suitable additional monomer is a non-ionic monomer or ionic monomer. If the monomer is ionic, it is either anionic or cationic. Additional monomers, when present, are preferably included in an amount of up to 10% by weight.

A preferred non-ionic monomer is a N-disubstituted acrylamide (preferably an N,N-dialkylacrylamide) or an analogue thereof. N,N-dimethylacrylamide (NNDMA) and/or an analogue thereof is particularly preferred.

A preferred cationic monomer is a quaternary ammonium salt. An especially preferred cationic monomer is (3-acrylamidopropyl)trimethyl ammonium chloride or [2-(acryloyloxy)ethyl]trimethyl ammonium chloride.

A preferred anionic monomer is an acrylate based monomer such as acrylic acid or a salt or ester thereof.

Plasticiser

The compositions according to the invention generally comprise, in addition to a crosslinked polymeric network, an aqueous plasticising medium and, optionally, additional electrolyte. Plasticisers are generally used in the invention to control adhesive properties.

The aqueous plasticising medium optionally additionally comprises a polymeric or non-polymeric polyhydric alcohol (such as glycerol), an ester derived therefrom and/or a polymeric alcohol (such as polyethylene oxide). Glycerol is the preferred plasticiser. An alternative. preferred plasticiser is an ester derived from boric acid and a polyhydric alcohol (such as glycerol). The aqueous reactive mixture preferably comprises from 10% to 50%, preferably from 10% to 45%, of plasticiser (other than water) by weight of the mixture.

It is well known that water in hydrogels can be present in at least two forms, freezing and non-freezing, as measured by Differential Scanning Calorimetry. In many examples of commercially available hydrogels the water is present only as non freezing water. It has been found, however, that compositions with useful adhesive properties comprising the first and second monomers can be made which have both freezing and non-freezing water, and the water activity in such gels is generally high. One advantage of including the second monomer is that it has a tendency to increase the likelihood that the compositions will contain freezing water. The advantage gained by the presence of freezing water becomes evident in the application of these gels to stress monitoring ECG. In certain cases the preferred medium for interfacing the monitoring instrument with the body is a "wet gel". It has been suggested that the advantage gained by "wet gels" is in the wetting of the skin and consequent lowering of skin impedance, but it has been found in clinical trials that hydrogels with freezing water can match the performance of "wet gels".

Interpenetrants

The compositions preferably additionally comprise a water soluble polymer suitable for forming an interpenetrating polymer network. Hydrogels based on interpenetrating polymer networks (IPN) are well known. An IPN has been defined as a combination of two polymers, each in network form, at least one of which has been synthesised and/or crosslinked in the presence of the other. As will be appreciated, this combination will generally be a physical combination rather than a chemical combination of the two polymers. IPN systems may be described by way of example as follows:

Monomer 1 is polymerised and crosslinked to give a polymer which is then swollen with monomer 2 plus its own crosslinker and initiator.

If only one polymer in the system is crosslinked the network formed is called a semi-IPN. Although they are also known as IPN's, it is only if there is total mutual solubility that full interpenetration occurs. In most IPN's there is, therefore, some phase separation but this may be reduced by chain entanglement between the polymers. It has also been reported that semi IPN's can be made in the presence of carrier solvents (for example water in the case of hydrophilic components).

It has been found that polymerising and crosslinking water soluble monomers in the presence of water soluble polymers, water and polyhydric alcohols produces hydrogel materials with enhanced rheological and consequently adhesive properties.

Suitable water soluble polymers for the formation of semi IPN's include poly (2-acrylamido-2-methylpropanesulphonic acid) or one of its salts and its copolymers, poly(acrylic acid-(3-sulphopropyl) ester potassium salt), copolymers of NaAMPS and SPA, polyacrylic acid, polymethacrylic acid, polyethylene oxide, polyvinyl methyl ether, polyvinyl alcohol, polyvinylpyrrolidone, its copolymers with vinyl acetate, dimethylaminoethyl methacrylate, terpolymers with dimethylaminoethyl methacrylate and vinylcaprolactam, polysaccharides such as gum arabic, karaya gum, xanthan gum, guar gum, carboxymethyl cellulose (CMC), NaCMC, hydroxypropylmethyl cellulose (HPMC), hydroxyethyl cellulose (HEC) or combinations thereof.

The amount of interpenetrant polymer used will be dependent on the mechanical and rheological properties required as well on consideration of processing conditions. If the interpenetrant polymer used increases the viscosity of the pre-gel mix beyond 5000 centipoise it has been found that the monomers do not polymerise and crosslink on an acceptable time scale (should be less than 60 seconds, preferably less than 10 seconds). The viscosity depends on the nature and molecular weight of the interpenetrant and the nature of pre-gel processing.

Of the natural polysaccharides, gum arabic or maltodextrin is usually preferred due to its cold water solubility and lesser effect on viscosity compared with, for example, karaya gum. A higher concentration of gum arabic than karaya may therefore be used if desired, enabling a wider control of hydrogel properties. It has also been found that the processing steps for assembling the pre-gel formulation can be critical with respect to the properties of the manufactured hydrogel. For a given formulation, if the components are assembled at 25° C. and cured different electrical and adhesive properties are obtained compared to those that have been heated to 70° C. Whilst adhesive properties may be enhanced, electrical properties e.g. low frequency impedance, can be downgraded. Solutions containing natural polysaccharides become less opaque indicative of improved solubility. The activity of water in compositions prepared from heat treated pre-gels generally is lower than in non heat treated pre-gels.

Other Additives

The composition preferably comprises a hydrophobic polymer. Hydrophobic polymers may be incorporated either in the presence or absence of interpenetrant polymers to form phase separated materials. The preparation of two phase composites consisting of a hydrophilic polymer containing an ionically conducting continuous phase and domains of a hydrophobic pressure sensitive adhesive which enhance adhesion to mammalian skin have been reported in U.S. Pat. No. 5,338,490. The method of preparation described therein involved casting a mixture (as a solution and or suspension) consisting of the hydrophilic polymer containing phase and hydrophobic components onto a substrate and then removing the solvent. It has been found, however, that adhesive ironically conducting hydrogels may be better prepared by combining the hydrophobic polymer (preferably as an emulsion) with the components of the pre-gel reaction mixture and casting these onto a substrate and curing. In other words, there is no need to remove a solvent in order to form useful materials. Furthermore, the hydrophilic phase of the composition in addition to being a crosslinked network may also be an IPN or semi IPN.

It is believed that when hydrophobic polymers are incorporated in this way that the hydrophobic component segregates to the surface (as determined by Fourier transform infrared attenuated total reflectance spectroscopy, FTIR ATR, approximate sampling depth 1 $\mu$m using a ZnSe crystal or 0.25 $\mu$m with a Germanium crystal) and that it is the amount of the hydrophobic component present in the surface that influences the adhesion to a wide variety of materials. The greater the amount of the hydrophobic component in the surface the greater the adhesion. In U.S. Pat. No. 5,338,490 weight ratios of the hydrophilic phase to the hydrophobic phase of 60:1 to 8:1 were claimed. In hydrogel adhesives of between 100 to 2000 microns thick made in accordance with the present invention, ratios of hydrophilic to hydrophobic components ranging from 7:1 to 1:20 have been found to be preferable, especially when these ratios are present in the surface of the adhesive composition. In the process of the present invention, however, it may take up to 72 hours from the initial curing of the adhesive hydrogel for the segregation of the hydrophobic materials to the surface, as defined by the ATR sampling depth, to be complete.

Preferably, the hydrophobic pressure sensitive adhesive in such embodiments is selected from the group consisting of polyacrylates, polyolefins, silicone adhesives, natural or synthetically derived rubber base and polyvinyl ethers or blends thereof. Preferably the hydrophobic pressure sensitive adhesive in these embodiments is an ethylene/vinyl acetate copolymer such as that designated DM137 available from Harlow Chemicals or vinyl acetate dioctyl maleate such as that designated Flexbond 150 and sold by Air Products. Those skilled in the art will also know that the molecular weight and comonomer ratios may be altered to control the properties of hydrophobic pressure sensitive adhesives. In general, the degree of surface segregation exhibited by such hydrophobic pressure sensitive adhesive (HPSA) will be dependent on factors such as composition of the HPSA, viscosity of the pre-gel mixture, temperature and rate of curing.

Surfactant

The composition according to the invention optionally includes a surfactant.

Any compatible surfactant may be used. Nonionic, anionic and cationic surfactants are preferred, either alone or in combination. The surfactant is preferably included in an amount from 0.1% to 20% by weight, more preferably 0.1% to 10% by weight.

In certain circumstances the reaction mixture preferably comprises from 3% to 20%, and more preferably from 8% to 18% by weight of the reaction mixture, of a stabilised polymer dispersion that is used to provide a stable phase separated system. The polymer preferably comprises any of the following either alone or in combination: vinylacetate dioctyl maleate copolymer or ethylene-vinyl acetate copolymer. Ethylene-vinylacetate copolymer is preferred, such as that marketed under the trade name DM137 by Harlow Chemicals.

The adhesive is thus typically formed by polymerising an aqueous reaction comprising from 5 to 50%, preferably from 30% to 50% by weight of the reaction mixture, of hydrophilic monomer, i.e. an ionic water soluble monomer, from 10% to 50%, preferably from 15% to 45% by weight of the reaction mixture, of a plasticiser (other than water), from 10% to 50%, preferably from 15% to 30% more preferably from 15% to 25% by weight of the reaction mixture, of a hydrophobic nonionic monomer, i.e. nonionic water soluble monomer, from 3 to 40%, by weight of the reaction mixture, of water.

In preparing adhesive compositions for use in the invention, the ingredients will usually be mixed to provide a reaction mixture in the form of an initial pre-gel aqueous based liquid formulation, and this is then converted into a gel by a free radical polymerisation reaction. This may be achieved for example using conventional thermal initiators and/or photoinitiators or by ionizing radiation. Photoinitiation is a preferred method and will usually be applied by subjecting the pre-gel reaction mixture containing an appropriate photoinitiation agent to UV light after it has been spread or coated as a layer on siliconised release paper or other solid substrate. The incident UV intensity, at a wavelength in the range from 240 to 420 nm, is ideally substantially 40 mW/cm$^2$. The processing will generally be carried out in a controlled manner involving a precise predetermined sequence of mixing and thermal treatment or history.

The UV irradiation time scale should ideally be less than 60 seconds, and preferably less than 10 seconds to form a gel with better than 95% conversion of the monomers and for conversion better than 99.95% exposure to UV light less than 60 seconds and preferably less than 40 seconds is preferred. Those skilled in the art will appreciate that the extent of irradiation will be dependent on the thickness of the reaction mixture, concentration of photoinitiator and nature of substrate on to which the reaction mixture is coated and the source of UV.

These timings are for medium pressure mercury arc lamps as the source of UV operating at 100 W/cm. The intensity of UV @ 254 nm and 313 nm reaching the surface of the substrate is approximately 150 $\mu$W/cm$^2$ and 750 $\mu$W/cm$^2$. For a given lamp UV intensity in a function of the operating power and distance of the reaction mixture from the UV source.

In order to minimize and preferably eliminate the presence of any residual monomers it is important to ensure that the reaction is complete. This is dependent upon a number of factors such as the substrate onto which the adhesive is applied, the type and intensity of the ultra violet light and the number of ultra violet light passes. Preferably the conversion of the hydrophilic monomers present such as NaAMPS should be 98%, preferably 99.0% most preferably 99.9% so that the amount of monomer within the adhesive is 4600 microg/g or less, preferably 2300 microg/g or less, most preferably 230 microg/g or less.

The adhesive is provided, typically on at least a portion of the wearer facing surface of the article, as a layer having a thickness or calliper C that is preferably constant, or that alternatively can vary over the surface of application of the adhesive.

When considering particularly the removal phase of an adhesive composition for attachment to the skin of a wearer, it is commonly recognised that good conditions of removal, i.e. at a frequency of about 100 rad/sec, of the adhesive applied to at least part of the wearer facing surface of the article, are achieved when the adhesive can be easily removed from the skin, and particularly from the bodily hair that may be, located on this area of the skin, where the article contacts the body, without causing pain to the wearer, therefore without adhering too hard upon removal, to the skin and the hair of the wearer. Moreover, a good removal implies that the adhesive does not leave residues on the skin or on the hair. The relationship between the thickness or calliper C measured in millimeters (mm) of the layer of the adhesive typically onto at least part of the wearer's facing surface of the absorbent article and the viscous modulus $G''_{25}$ at 25° C. at about 100 rad/sec of the adhesive gives an indication of painless and easy removal of the adhesive from the skin.

Without being bound to any theory, it is believed that for higher values of $G''_{25}$ at 100 rad/sec, which overall correspond to a higher adhesiveness of the composition, a thicker calliper or thickness C of the adhesive layer is needed so that the energy applied for the removal is more evenly distributed within the mass of the adhesive, and is therefore transferred smoothly to the skin, so avoiding peaks of energy that typically cause the pain sensation to the wearer. In other words, thinner layers of the adhesive necessitate an adhesive with a lower $G''_{25}$ at 100 rad/sec to achieve a reduced pain sensation upon removal of the article.

According to the present invention, the adhesive is preferably provided as a layer having a thickness C such that the viscous modulus $G''_{25}$ (100 rad/sec) and the thickness C of the adhesive layer satisfy the following empirical equation:

$$G''_{25} \leq [(7.00+C) \times 3000] Pa$$

and preferably the following empirical equation:

$$G''_{25} \leq [(5.50+C) \times 1700] Pa$$

While in a preferred embodiment of the present invention the thickness C of the adhesive layer is constant, such an adhesive layer can also have different thicknesses in different portions of the wearer facing surface where it is applied, provided that the above mentioned relationship between C and $G''_{25}$ is in any case satisfied in each portion.

In order to evaluate the effect of the thickness C of the adhesive layer in its relationship with the viscous modulus $G''_{25}$ (100 rad/sec) of the adhesive of the present invention on the removal of the adhesive used for the attachment of a article to the skin of a wearer, a Removal Pain Grade Test has been developed. In this test the adhesion of standard substrates, on which the same adhesive has been provided in layers having different thicknesses, on the skin of the forearm of members of a sensory panel is achieved, and upon successive removal the pain is evaluated in terms of pain grade as described herein after.

DESCRIPTION OF THE DISPOSABLE ABSORBENT ARTICLE

Absorbent articles in association with which the adhesive as defined herein can be used, can be made by any of the ways usual in the art. The application of the adhesive to the wearer facing surface, typically the topsheet surface of an absorbent article should not cause major problems to those skilled in the art since it can be provided by any well known techniques commonly used to apply adhesives. Most preferably the adhesive is provided in a pattern of small incremental areas such as dots or similar.

The adhesive is applied on at least portion of the wearer facing surface of disposable absorbent articles in a layer having a thickness or caliper that is preferably constant, or that alternatively can vary over the surface interested by the application of the adhesive. The adhesive can be applied to the wearer facing surface of the article by any means known in the art such as slot coating, spiral or bead application or printing. Typically the adhesive is applied at a basis weight of from 20 $g/m^2$ to 2500 $g/m^2$, preferably from 500 $g/m^2$ to 2000 $g/m^2$, most preferably from 700 $g/m^2$ to 1500 $g/m^2$ depending in the end use envisioned.

If possible, the article also provides breathability by being at least water vapour permeable, preferably air permeable to prevent stuffiness. Breathability, if not supported by the adhesive as such, can be limited to the area of the article where no adhesive is applied.

The adhesive on an article is preferably protected prior to use. This protection can be provided by a release liner such as a siliconised or surfactant treated paper, providing easy release for the selected adhesive.

This invention can be used beneficially on disposable absorbent articles which are applied directly to the skin of a user. The article usually exhibits absorbency for bodily fluids, the protection of the user's garments from soiling, is comfortable to the user, and is easy to produce and to package. The disposable absorbent article is described below by reference to a sanitary napkin or catamenial, however diapers, panty liners, adult incontinence articles, tampons or perspiration pads are also included under the term disposable absorbent articles. The term "sanitary napkin", as used herein, refers to an article which is worn by females adjacent to the pudendal region and which is intended to absorb and contain the various body fluids which are discharged from the body (e.g., vaginal discharges, menses, and/or urine) and which is intended to be discarded after a single use. A disposable absorbent article is preferably thin, more preferably between 1 and 5 mm thick and either substantially flat prior to use or in a preshaped form.

The terms "joined" or "affixed", as used herein, encompasses configurations whereby a first member is directly connected to a second member and configurations whereby a first member is indirectly connected to a second member by connecting the first member to intermediate members which in turn are connected to the second member.

The sanitary napkin has two main surfaces, a body contacting or wearer facing surface on which the adhesive is applied and a garment facing or contacting surface. In a one preferred embodiment a sanitary napkin of the present invention comprises a liquid pervious topsheet, a liquid impervious backsheet joined to the topsheet, and an absorbent core intermediate the topsheet and the backsheet. In an alternative embodiment, the sanitary napkin or panty liner may utilize the adhesive to absorb quantities of liquid up to amounts of about 10 g, such that a separate core and topsheet are not required. Such products preferably have a backsheet as described below.

The topsheet is compliant, soft feeling, and non-irritating to the wearer's skin. The topsheet also can have elastic characteristics allowing it to be stretched in one or two directions in portions of the topsheet or throughout its extension. Further, the topsheet is fluid pervious permitting fluids (e.g., menses and/or urine) to readily penetrate through its thickness.

Preferred topsheets for use in the present invention are typically selected from high loft nonwoven topsheets and apertured formed film topsheets. Apertured formed films are especially preferred for the topsheets because they are pervious to body exudates and yet non absorbent and have a reduced tendency to allow fluids to pass back through and rewet the wearer's skin. Thus, the surface of the formed film that is in contact with the wearer remains dry, thereby reducing body soiling and creating a more comfortable feel for the wearer. Suitable formed films are described in U.S. Pat. Nos. 3,929,135; 4,324,246; 4,342,314; 4,463,045; and 5,006,394. Particularly preferred micro apertured formed film topsheets are disclosed in U.S. Pat. Nos. 4,609,518 and 4,629,643. A preferred topsheet for the present invention comprises the formed film described in one or more of the above patents and marketed on sanitary napkins by The Procter & Gamble Company of Cincinnati, Ohio as "DRI-WEAVE".

Adhesives are most suitably used on topsheets having not a homogeneous distribution of liquid passage ways but only a portion of the topsheet comprising liquid passage ways oriented such that they result in a centrally permeable and peripherally impermeable topsheet for liquids.

Another alternative are so called hybrid topsheets which incorporate fibrous and film like structures particularly useful embodiments of such hybrid topsheets are disclosed in PCT publications WO 93/09744; WO 93/11725 or WO 93/11726.

When referring to the topsheet a multi layer structure or a mono layer structure is contemplated. The hybrid topsheet mentioned above is such a multi layer design but other multi layer topsheets such as primary and secondary topsheet designs are also considered.

The absorbent core also can comprise multiple layers and provides fluid storage and distribution function.

Positioned in fluid communication with, and typically underlying the topsheet is the absorbent core. The core can comprise any usual absorbent material or combinations thereof. It preferably comprises absorbent gelling materials usually referred to as "hydrogel", "superabsorbent", "hydrocolloid" materials in combination with suitable carriers.

Suitable absorbent gelling materials for use herein will most often comprise a substantially water-insoluble, slightly cross-linked, partially neutralised, polymeric gelling material. This material forms a hydrogel upon contact with water. Such polymer materials can be prepared form polymerizable, unsaturated, acid-containing monomers, such as acrylic acid, which are well known in the art.

Suitable carriers include materials which are conventionally utilised in absorbent structures such as natural, modified or synthetic fibers, particularly modified or non-modified cellulose fibers, in the form of fluff and/or tissues. Suitable carriers can be used together with the absorbent gelling material, however, they can also be used alone or in combinations. Most preferred are tissue or tissue laminates in the context of sanitary napkins/panty liners.

An embodiment of the core, particularly useful in the application of the present invention, comprises a double layer tissue laminate formed by folding the tissue onto itself. These layers can be joined to each other. Absorbent gelling material or other optional material can be comprised between the layers.

The absorbent core can include optional components normally present in absorbent webs such as odor control agents, in particular suitable zeolites.

The backsheet primarily prevents the exudates absorbed and contained in the absorbent core from wetting articles that contact the absorbent product such as underpants, pants, pyjamas and undergarments. The backsheet is preferably impervious to liquids (e.g. menses and/or urine) and usually manufactured from a thin plastic film.

The backsheet typically extends across the whole of the absorbent core and can extend onto and form part of the topsheet by folding around the absorbent core. Thereby a topsheet configuration as disclosed in U.S. Pat. No. 4,342,314, column 16, lines 47–62 can be achieved without the requirement to selectively aperture the topsheet.

Preferably, the backsheet also provides breathability to the absorbent article by being at least water vapour permeable, preferably air permeable. The backsheet can be a laminate material e.g. of a combination of microporous film and/or non-woven material, and/or apertured formed film. Breathability if desired can be limited to the periphery or the center of the backsheet or it can be across the whole backsheet.

According to the present invention the adhesive as described herein may also find application to attach other articles to the skin. The adhesives may for example find utility to adhere functional articles which adhere to the skin such as cosmetic or pharmaceutical delivery articles which provide a substance to the skin such as skin treatment substances, cream, lotions, hormones, vitamins, deodorants, drugs; cosmetic or pharmaceutical delivery articles provide a substance to emanate away from the skin such as insecticides, inhalation drugs, perfumes and; functional articles which are not necessarily attached to the skin, but which require a high residence time on the skin such as decorative cosmetics, (lipstick, eye shadow, stage make-up) and cleaning articles (hand cleaners, face masks and hygienic pore cleansers). Such articles are preferably non-absorbent for bodily liquids.

The adhesive may also in addition find application to attach articles to the skin such as protective articles such as genital-, knee- or elbow-protectors or bandages; clothing such as bras, surgical gowns, or parts of garments during fitting at a tailor; nasal plasters; prosthesis such as breast replacements or wigs; cold wraps e.g. to provide pain relief from bruises and to reduce swelling; thermal wraps comprising thermal cells as disclosed for example in WO97/36968 and WO97/49361 to provide relief of temporary and chronic pain such as neck wraps as disclosed in for example U.S. Pat. No. 5,728,146, knee wraps exemplified in WO97/01311, and back wraps as disclosed for example in U.S. Pat. No. 5,741,318; hearing aids; protective face masks (for the reduction or prevention of inhalation of noxious substances); ornamental articles such as jewelry, earrings, guises, tattoos; goggles or other eye wear; ostomy devices, tapes, bandages, dressings of general utility, wound healing and wound management devices; and biomedical skin electrodes such as ECG, EMG, EEG, TENS electrosurgery, defibrillation, EMS and electrodes for facial/beauty applications; and fixation products and/or devices intended to affix patient catheters, tubing leadwires cables etc.

Removal Pain Grade Test

The Removal Pain Grade Test is utilized to evaluate the pain during removal from the skin of a wearer of a sample provided with a layer of a adhesive and previously attached to the wearer's skin. The test specifically evaluates the pain upon removal of each sample as compared to the pain obtained by removing a reference sample constituted by a commercial strong medical plaster.

Sample preparation

The test is performed on rectangular samples 60×20 mm made of a polyester film 23 $\mu$m thick, such as that sold by Effegidi S.p.A. of Colorno (Parma, Italy), provided on one side with a continuous layer of the adhesive having the selected thickness. The reference sample is a 60×20 mm sample of an adhesive non woven fabric available from Beiersdorf A. G. Hamburg, Germany under the Tradename Fixomull stretch Test method A panel of six graders is selected for the test. The test is performed in a climatically controlled laboratory maintained at a temperature of 23° C. and a Relative Humidity of 50%. No special treatment of the wearer's skin is required beyond normal cleaning/washing with water and soap. The skin is then allowed to dry for at least two hours before the test to allow the skin to reach equilibrium with the room conditions. Different adhesive are evaluated in the test in comparison with the reference sample R. Each sample is applied by hand by an operator to the inner part of the grader's forearm, being centred between the wrist and the elbow, with the short side of the sample aligned with the length of the arm. The operator exerts on each sample with the palm of the hand the same pressure that is typically applied to cause a medical plaster to adhere to the skin. Each sample is worn for the prescribed time, and then it is removed from the grader's skin by the operator with a slow and smooth pull.

Four series of one reference sample R and the test samples are each applied, worn and then removed from the wearer's skin; each sample is worn for one minute, with a 5 minute wait between two subsequent samples of the same series, and a 15 minute wait between two different subsequent series. The reference sample R is always applied, worn and removed as the first sample of its respective series. The sequence of application/wear/removal of the test samples in each of the first three series is random, provided that no repetition in each series is allowed, and that no sequence is repeated in the first three series. In the fourth series one of the test samples is tested twice, the reference R always being the first one. Overall each sample has to be tested an equal number of times (24 times).

The graders were asked to evaluate each sample using a pain scale ranging from 0 to 10, where 0 corresponds to no pain and 10 corresponds to the pain upon removal of the reference sample R. The pain values for each sample were obtained as a mean of 24 observations.

The results collected from the test were analysed by a statistical analysis program "Comparison of Population Means—Paired Samples", that showed that the differences between the pain values of the samples are statistically significant.

Peel Adhesion Method

This is a quantitative method to determine the average peel force required to remove a skin at a specified peel angle and speed.

Equipment

| | |
|---|---|
| Scissors | Convenient source |
| Standard ruler | Convenient source |
| Steel Roller | 5.0 kg Mass. 13 cm in diameter and 4.5 cm in width covered with 0.5 mm thick rubber. |
| Polyester Film | PET 23$\mu$ available from EFFEGIDI S.p.A., 43052 Colorno, Italy. |
| Transfer Adhesive | 3M 1524 available from 3M Italia S.p.a., 20090 Segrate Italy |
| Stop watch | Convenient source |
| Tensile Tester | Instron mod.: 6021 (or equivalent) |

Test Procedure

A) Tensile Tester Peel Settings:

| | |
|---|---|
| Load cell | 10 N |
| Test Speed | 1000 mm/min |
| Clamp to Clamp distance | 25 mm |
| Pre Loading | 0.2 N |
| Test Path "LM" | 50 mm |
| Measure variable | F average (N) in "LM" |

B) Skin Condition and Preparation

The sample is peel from the forearm. There are 3 conditions of the skin that are tested:
1) Dry: The forearm is untreated and not wiped prior to test or between repetitions.
2) Wet: To one cotton disk (Demak' up diameter 5.5 cm, weight about 0.6 g), 3 ml of distilled water is added. Next the disk is then wiped with a light pressure 3 times over the test area on the forearm. (The test area of the forearm is a rectangle approximately 2 cm wider and longer than the adhesive area).

C) Sample Preparation
1. Allow the samples to adjust to conditioned room (23±2° Celsius and 50±2%RH) for about 1 hr.
2. Prepare rectangular adhesive samples 260 mm ±2 length and 20 mm ±2 wide.
3. Attach on the sample surface the polyester film (using the transfer adhesive to attach the polyester to the substrate surface).
4. Each test specimen should be prepared individually and tested immediately.
5. Remove the release paper from the adhesive without touching it. Attach one end to the skin (see section B).
6. Roll the Steel Roller for 160 mm along the adhesive strip, once in each direction.

D) Test Environment

There are 2 environments the adhesive can be tested in:
1) Conditioned Room as described in C1.
2) Wet Environment. Here, after step C4, the specimen is taken and put in a humidity controlled oven for 3 hours at 85 deg C. It is then taken out and steps C5, C6 are carried out.

E) Execution 1 minute after Step C6, take the free end of the specimen (approx. 100 mm long) and insert it in the upper end of the adhesion testing machine. Ensure the specimen is at a 90 degree angle to the forearm. Start the testing machine.

F) Report

Report the average of the peel strength of 5 tests. The single values are the base to calculate the standard deviation between the samples.

Residual Monomer Test Method

Test Sample 1 gram of a hydrogel sample is taken and emersed in 100 ml 0.9% saline water.

The sample is left in the saline at 40 deg C. for 24 hours.

An aliquot of the liquid is diluted and analysed by electrospray LC/MS/MS.

Calibration Sample 1 gram of reference monomers (eg NaAmps) are dissolved in 100 ml 0.9% saline water.

An aliquot of the liquid is diluted and analysed by electrospray LC/MS/MS.

Evaluation

The concentration of the test and calibration sample are determined by linear regression analysis using a software package such as VG Mass Lynx.

Adhesive Preparation

Suitable adhesives were prepared as described in the following Examples.

EXAMPLE 1

In 20 parts of polyethylene glycol diacrylate (pEG600) (product of UCB Chemicals marketed under the trade name designation of Ebacryl 11) were dissolved 6 parts of 1-hydroxycyclohexyl phenyl ketone (product of Ciba and marketed under the trade name designation of Irgacure 184). The solution so produced is herein designated solution A (XL/PI). Separately, 50 parts of the potassium salt of 3-sulphopropyl acrylate (SPA) (product of Raschig) were dissolved in 50 parts water to form solution B. A further solution designated solution C consisted of 50 parts water, 50 parts of the sodium salt of 2-acrylamido-2-methylpropane sulphonic acid (NaAMPS) product of the Lubrizol Corporation and marketed as a 50% aqueous solution under the trade name LZ2405). Mixtures of solutions B and C in the ratios of 100:0, 90:10, 60:40, 50:50, 40:60, 10:90 and 0:100 were made to form pre-gel solutions. To 80 parts of each of these pre-gel solutions, 0.15 parts of solution A, 5 parts potassium chloride and 20 parts distilled water were added. The pre-gel solutions were coated onto siliconised release paper at a coat weight of 0.8 kilograms per square meter and exposed to ultraviolet radiation by being passed under a medium pressure mercury arc lamp at a speed of 5 meters per minute to form clear self supporting gels. The residence time under the lamp was 4 seconds. The storage moduli(G') of 20 mm diameter discs stamped from the gels were recorded on a Rheometric Scientific RS-5 rheometer at 37° C. The G' values at 1 rad are recorded in Table 1. With the exception of the gels containing 90 and 100 parts SPA, the gels produced had acceptable tack and peel properties on the skin. From the data in Table 1 relatively linear changes in storage modulus are obtained on increasing or decreasing the SPA to NaAMPS ratio.

In the above Example, and in the following Examples wherever parts are mentioned they are meant as parts by weight unless otherwise specified.

TABLE 1

| NaAMPS SolutionC | 80 | 72 | 48 | 40 | 32 | 8 | 0 |
|---|---|---|---|---|---|---|---|
| SPA SolutionB | 0 | 8 | 32 | 40 | 48 | 72 | 80 |
| Distilled Water | 20 | 20 | 20 | 20 | 20 | 20 | 20 |
| XL/PI SolutionA | 0.15 | 0.15 | 0.15 | 0.15 | 0.15 | 0.15 | 0.15 |
| KCI | 5 | 5 | 5 | 5 | 5 | 5 | 5 |
| G'(Pa) @ 1 rad/s | 4,198 | 3,389 | 2,471 | 2,205 | 1,759 | 703 | 492 |

EXAMPLE 2

In 20 parts of polyethylene glycol diacrylate (pEG600) (product of UCB Chemicals marketed under the trade name designation of Ebacryl 11) 6 parts of 1-hydroxycyclohexyl phenyl ketone (product of Ciba and marketed under the trade name designation of Irgacure 184) were dissolved. (This solution is designated solution A) (XL/PI). Separately 58 parts of the potassium salt of 3-sulphoproylacrylate (SPA) (product of Raschig) were dissolved in 58 parts distilled water to form solution D. A further solution designated solution E consisted of 42 parts water, 58 parts of the sodium salt of 2-acrylamido-2-methylpropane sulphonic acid (NaAMPS) (a product of the Lubrizol Corporation marketed as a 58% aqueous solution under the trade name LZ2405A). Mixtures of solutions D and E in the ratios 100:0, 90:10, 60:40, 50:50, 40:60, 10:90 and 0:100 were made to form pre-gel solutions. To 100 parts of each of these pre-gel solutions, 0.17 parts of solution A and 3 parts potassium chloride were added. The pre-gel solutions were coated onto siliconised release paper at a coat weight of 0.8 kilograms per square meter and passed under a medium pressure mercury arc lamp at a speed of 5 meters per minute to form clear self-supporting gels. Storage moduli were measured as in Example 1 and are recorded in Table 2. As in the gels described in Example 1 the changes in the elastic or storage modulus G'(Pa) are linear with respect to the increasing or decreasing ratio of NaAMPS to SPA. All the gels produced possess acceptable tack and peel strength against skin. The gels with NaAMPS:SPA ratios in the range of 60:40 to 40:60, however, have a better balance of reusability and peel strength.

TABLE 2

| NaAMPS SolutionE | 100 | 90 | 60 | 50 | 40 | 10 | 0 |
|---|---|---|---|---|---|---|---|
| SPA SolutionD | 0 | 10 | 40 | 50 | 60 | 90 | 100 |
| XL/PI SolutionA | 0.17 | 0.17 | 0.17 | 0.17 | 0.17 | 0.17 | 0.17 |
| KCI | 3 | 3 | 3 | 3 | 3 | 3 | 3 |
| G'(Pa) @ 1 rad/s | 15,142 | 14,333 | 11,073 | 10,672 | 9,920 | 6,280 | 5,199 |

Upon varying the amount of the cross-linking agent a substantially linear change in the elastic modulus G' can also be obtained, as illustrated by the graph of FIG. 1.

EXAMPLE 3

To 57 parts of a 58% solution of the sodium salt of 2-acrylamido-2-methylpropane sulphonic acid (NaAMPS) (LZ2405A) 10 parts of a 58% solution of the potassium salt of 3-sulphopropyl acrylate (SPA) were added along with 5 parts potassium chloride and stirred until the potassium chloride has dissolved. This solution was then mixed with 30 parts glycerol for 30 minutes. To the latter solution were added 0.15 parts of a solution containing 20 parts of polyethylene glycol diacrylate (pEG600) (product of UCB Chemicals marketed under the trade name designation of Ebacryl 11) in which 6 parts of 1-hydroxycyclohexyl phenyl ketone (product of Ciba and marketed under the trade name designation of Irgacure 184) were dissolved. The soformed pregel solution was then cured as in Example 1. Good skin adhesion properties were obtained for this gel.

EXAMPLE 4

To 34.7 parts of a 58% aqueous solution of the sodium salt of 2-acrylamido-2-methylpropane sulphonic acid (NaAMPS) (LZ2405A) 34.7 parts of a 58% aqueous solution of the potassium salt of 3-sulphoproyl acrylate (SPA) were added along with 4.6 parts potassium chloride and 3 parts distilled water and stirred until the potassium chloride has dissolved. This solution was then mixed with 23.2 parts glycerol for 30 minutes. To the latter solution were added 0.15 parts of solution A prepared as described in Example 1. The so-formed pre-gel solution was then cured as in Example 1.

EXAMPLE 5

To 20 parts glycerol, 3 parts of a hydrophobic ethylene/vinyl acetate copolymer emulsion (50% solids) (product of Harlow Chemicals marketed under the trade name DM137) and 10 parts polyethylene glycol (molecular weight 600) were added and stirred until a uniform colour was obtained. To this mixture were added 50 parts of a 58% solution of the sodium salt of 2-acrylamido-2-methylpropane sulphonic acid (NaAMPS) (LZ2405A), 16 parts potassium salt of 3-sulphopropyl acrylate (SPA) and 5 parts potassium chloride, and the solution was heated with stirring to 60° C. for one hour. The mixture had changed from an opaque off white to a translucent off white appearance. The turbidity of the solutions as measured in a portable turbidity meter, product code H193703 marketed by Hanna had changed from 254 ftu to 107 ftu. The solution was cooled to 20° C. and then there was added 0.13 parts of solution A prepared as described in Example 1. This final solution was stirred for one hour and then cured as in Example 1. The resulting gel had a G' value at 1 rad of 5328 Pa. The activity of water in the gel, as determined by placing the gel into cabinets at varying levels of humidity at 40° C. (40, 52, 64 and 80%RH) and measuring weight uptake or loss and extrapolating to zero weight change, was 0.62. The adhesion to skin of this gel was significantly greater than those described in the previous examples. Analysis of the gel by attenuated total reflectance infra-red spectroscopy revealed that in the surface regions (about 1 micron or less), either the air surface or the surface in contact with the release paper, the concentration of the ethylene/vinyl acetate copolymer relative to the NaAMPS was significantly enhanced compared to the bulk composition.

EXAMPLE 6

The method of Example 5 was carried out except that with the glycerol were added 3 parts of gum arabic. The resulting gel had a G' value at 1 rad of 5406Pa. The activity of water as determined by the method in Example 5 was 0.55. The adhesion to skin of this gel was significantly greater than those described in the previous examples. Analysis of the gel by attenuated total reflectance infra-red spectroscopy revealed that in the surface region (about 1 micron or less), either the air surface or the surface in contact with the release paper, the concentration of the ethylene/vinyl acetate copolymer relative to the NaAMPS was significantly enhanced compared to the bulk composition.

EXAMPLE 7

The formulations shown in Table 3 were prepared using the following method which is for formulation 7a. To 33 parts glycerol, 10 parts of a hydrophobic ethylene/vinyl acetate copolymer emulsion (50% solids) (product of Harlow Chemicals marketed under the trade name DM137) were added and stirred until a uniform colour was obtained. To this mixture were added 35 parts of a 58% solution of the sodium salt of 2-acrylamido-2-methylpropane sulphonic acid (NaAMPS) (LZ2405A) and 15 parts potassium salt of 3-sulphopropyl acrylate (SPA), and the solution was heated with stirring to 60° C. for one hour. The solution was cooled to 20° C. and then there was added 0.15 parts of solution A prepared as described in Example 1. This final solution was stirred for one hour and then cured as in Example 1.

To prepare formulation 7b the same method used for formulation 7a was repeated except that the parts by weight were changed to the figures given in Table 3.

To prepare formulation 7c the same method used for formulation 7a was repeated except that a propylene oxide/ethylene oxide block copolymer surfactant (designated PE/F127 and manufactured by BASF) was added with the glycerol and the parts by weight were changed to the figures given in Table 3.

TABLE 3

| | COMPOSITION by WEIGHT | | |
|---|---|---|---|
| Formulation | 7a | 7b | 7c |
| 58% NaAMPS | 35 | 35 | 35 |
| SPA | 15 | 25 | 25 |
| Glycerol | 33 | 20 | 20 |
| DM137 | 10 | 15 | 15 |
| PEG600 | 5 | 10 | 10 |
| PE/F127 | | | 1 |
| PI/XL (Solution) | 0.15 (A) | 0.14 (A) | 0.14 (A) |

As will be seen, the invention presents a number of different aspects and it should be understood that it embraces within its scope all novel and inventive features and aspects herein disclosed, either explicitly or implicitly and either singly or in combination with one another. Also, many detail modifications are possible and, in particular, the scope of the invention is not to be construed as being limited by the illustrative example(s) or by the terms and expressions used herein merely in a descriptive or explanatory sense.

What is claimed is:

1. A disposable absorbent article (10) comprising a wearing facing surface and a garment facing surface, said wearing facing surface comprising at least one portion comprising an adhesive, characterised in that said adhesive has:
   (i) a water activity of from 0.4 to 0.9;
   (ii) an elastic modulus at 1 rad/s of from 700 to 15,000 Pa;
   (iii) an elastic modulus at 100 rad/s of from 2000 to 40,000 Pa;
   (iv) a viscous modulus at 1 rad/s of from 450 to 14,000 Pa;
   (v) a viscous modulus at 100 rad/s of from 1000 to 35,000 Pa;
wherein the viscous modulus is less than the elastic modulus in the frequency range of from 1 to 100 rad/s.

2. A disposable absorbent article according to claim 1, wherein the adhesive comprises a hydrophobic polymer wherein the concentration of the polymer at the surface is greater than the concentration in the bulk of the adhesive.

3. An absorbent article (10) according to claim 1, wherein the adhesive comprises an aqueous plasticiser, a copolymer of a hydrophilic unsaturated water-soluble first monomer and a hydrophilic unsaturated water-soluble second monomer and a cross-linking agent, the first monomer having a tendency preferentially to enhance the bioadhesive properties of the composition.

4. An absorbent article (10) according to claim 1, wherein the adhesive is obtainable by polymerising an aqueous reactive mixture comprising a hydrophilic unsaturated water-soluble first monomer and a hydrophilic unsaturated water-soluble second monomer and a cross-linking agent, the first monomer having a tendency preferentially to enhance the bioadhesive properties of the composition.

5. An absorbent article (10) according to claim 4, wherein the first monomer has a tendency also to enhance the mechanical strength of the composition and/or the second monomer has a tendency preferentially to increase the water activity of the composition.

6. An absorbent article (10) according to claim 5, wherein the first monomer is a compound of formula

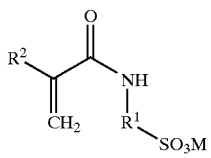

(I)

wherein $R^1$ is an optionally substituted hydrocarbon moiety, $R^2$ is hydrogen or optionally substituted methyl and ethyl, and M represents hydrogen or a cation.

7. An absorbent article (10) according to claim 6 characterized in that the second monomer is a compound of formula

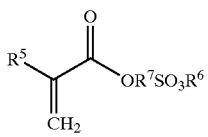

(II)

wherein $R^5$ represents hydrogen or optionally substituted methyl or ethyl, $R^6$ represents hydrogen or a cation and $R^7$ represents an optionally substituted alkylene moiety of 1 to 4 carbon atoms.

8. An absorbent article (10) according to claim 7, characterized in that the first monomer is 2-acrylamido-2-methylpropanesulphonic acid or an analogue thereof or one of its salts, and/or the second monomer is a polymerisable sulphonate or a salt of acrylic acid (3-sulphopropyl)ester or an analogue thereof.

9. An absorbent article (10) according to claim 8, wherein the ratio of the first monomer to the second monomer by weight is from 20:1 to 2:3.

10. An absorbent article (10) according to claim 9, wherein the aqueous reactive mixture further comprises a surfactant, an additional monomer, an electrolyte, a water soluble polymer suitable for forming an interpenetrating polymer network, a lipid-micellising polymer, a non-hydrophilic polymer, and/or an antimicrobial agent.

11. An absorbent article (10) according to claim 1, wherein said wearer facing surface of said article comprises at least one non-adhesive portion.

12. An absorbent article (10) according to claim 1, characterized in that said adhesive is provided as a continuous layer.

13. An absorbent article (10) according to claim 1 wherein said adhesive is applied to said wearer facing surface by slot coating.

14. An absorbent article (10) according to claim 1, wherein said article comprises a backsheet and said backsheet is in direct contact with said adhesive.

15. An absorbent article (10) according to claim 1, wherein said article comprises a topsheet, a backsheet and an absorbent core located in between said topsheet and said backsheet.

* * * * *

UNITED STATES PATENT AND TRADEMARK OFFICE
CERTIFICATE OF CORRECTION

PATENT NO.    : 6,613,030 B1
DATED         : September 2, 2003
INVENTOR(S)   : Coles et al.

It is certified that error appears in the above-identified patent and that said Letters Patent is hereby corrected as shown below:

Column 23,
Lines 8-9, "soformed pregel" should be -- so-formed pre-gel --

Signed and Sealed this

Seventh Day of September, 2004

JON W. DUDAS
*Director of the United States Patent and Trademark Office*